United States Patent [19]

Yukinaga et al.

[11] 4,212,981
[45] Jul. 15, 1980

[54] PROCESS FOR PREPARING 3-ISOXAZOLYLUREA DERIVATIVES

[75] Inventors: Hisajiro Yukinaga, Kusatsu; Shinzaburo Sumimoto; Ichiro Ishizuka, both of Osaka; Jitsuo Sugita, Ikeda, all of Japan

[73] Assignee: Shionogi & Co., Ltd., Osaka, Japan

[21] Appl. No.: 852,049

[22] Filed: Nov. 16, 1977

Related U.S. Application Data

[63] Continuation-in-part of Ser. No. 667,033, Mar. 15, 1976, Pat. No. 4,062,861, which is a continuation of Ser. No. 491,491, Jul. 23, 1974, abandoned.

[51] Int. Cl.$^2$ .......................................... C07D 261/14
[52] U.S. Cl. ................................... 548/246; 544/137; 544/367; 546/209
[58] Field of Search .................... 260/307 H, 307 DA; 544/137, 367; 546/209; 548/246

[56] References Cited

U.S. PATENT DOCUMENTS

3,073,839  1/1963  Kano et al. .................. 260/307 H

OTHER PUBLICATIONS

March, "Advanced Org. Chem." (1968), pp. 816–817.
Morrison et al., "Org. Chem." (1966), p. 927.
March, "Advanced Organic Chemistry," (1968) pp. 236–241.
Fieser, et al., "Reagents for Org. Syn." (1967), pp. 296–298, 310–311.

*Primary Examiner*—David Wheeler
*Attorney, Agent, or Firm*—Wenderoth, Lind & Ponack

[57] ABSTRACT

3-Isoxazolylurea derivatives of the formula:

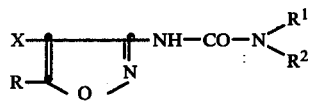

(wherein R represents hydrogen, $C_1$–$C_6$ alkyl, or $C_6$–$C_8$ aryl; $R^1$ represents hydrogen or $C_1$–$C_6$ alkyl; $R^2$ represents $C_1$–$C_6$ alkyl, $C_6$–$C_8$ aralkyl, or $C_6$–$C_8$ aryl; or

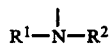

represents pyrrolidino, piperidino, morpholino, or 4-alkylpiperazino; X represents hydrogen or halogen; or R and X may optionally form $C_3$–$C_5$ alkylene), are prepared by reacting a carboxamide of the formula:

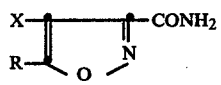

(wherein R and X each is as defined above) with an amine of the formula:

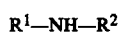

(wherein $R^1$ and $R^2$ each is as defined above) in the presence of an alkaline hypohalite and an alkaline hydroxide in an inert solvent medium.

10 Claims, No Drawings

PROCESS FOR PREPARING 3-ISOXAZOLYLUREA DERIVATIVES

This application is a continuation-in-part of Ser. No. 667,033, filed Mar. 15, 1976, now U.S. Pat. 4,062,861, which is a continuation of Ser. No. 491,491, filed July 23, 1974, now abandoned.

The present invention relates to a process for preparing 3-isoxazolylurea derivatives.

It has been discovered by the present inventors that the 3-isoxazolylurea derivatives show an excellent selective herbicidal activity [U.S. Pat. 4,062,861]. However, since said application discloses a process using isoxazolylamines as starting compounds which are prepared by reacting isoxazolyl ester with ammonia and reacting the resultant isoxazolylamide with an alkali hypohalite, it requires longer steps with insufficient yield.

As results of various investigations for overcoming the defects of said prior process, the present inventors have succeeded in developing the synthetic process of 3-isoxazolylurea in short steps using 3-carbamoylisoxazole derivatives as starting compounds.

The present invention relates to a process for preparing 3-isoxazolylurea derivatives of the formula:

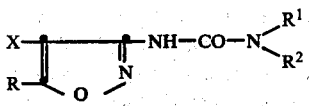

(wherein R represents hydrogen, $C_1$–$C_6$ alkyl, or $C_6$–$C_8$ aryl; $R^1$ represents hydrogen or $C_1$–$C_6$ alkyl; $R^2$ represents $C_1$–$C_6$ alkyl, $C_6$–$C_8$ aralkyl, or $C_6$–$C_8$ aryl; or

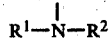

represents pyrrolidino, piperidino, morpholino, or 4-alkylpiperazino; X represents hydrogen or halogen; or R and X may optionally form $C_3$–$C_5$ alkylene), which comprises reacting a carboxamide of the formula:

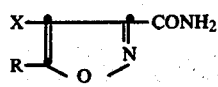

(wherein R and X each is as defined above) with an amine of the formula:

(wherein $R^1$ and $R^2$ each is as defined above) in the presence of an alkaline hypohalite and an alkaline hydroxide in an inert solvent medium.

The above definitions are illustratively explained as follows: alkyl (e.g. methyl, ethyl, propyl, i-propyl, butyl, i-butyl, t-butyl, cyclopropyl, cyclopentyl, cyclohexyl), aryl (e.g. phenyl, tolyl, xylyl), aralkyl (e.g. benzyl, phenethyl), alkylene (e.g. trimethylene, tetramethylene, pentamethylene), and halogen (e.g. chlorine, bromine, iodine).

The process of this invention is shown in the following scheme:

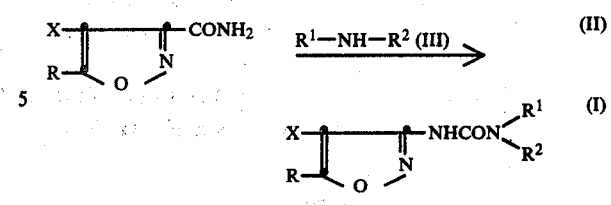

(wherein R, $R^1$, $R^2$, and X each is as defined above).

The starting carboxamide (II) can be prepared from the corresponding carboxlic acid (IV):

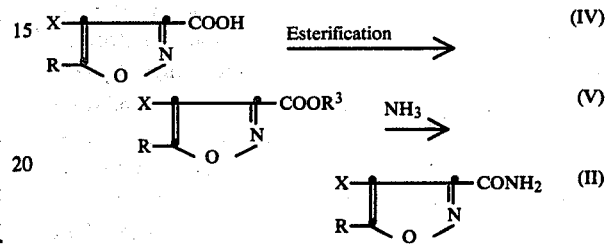

(wherein $R^3$ represents alkyl, and R and X each is as defined above) [Japanese Pat. No. 303,133].

The amine (III) illustratively involves a primary amine (e.g. methylamine, ethylamine, propylamine, butylamine, cyclohexylamine), and a secondary amine (e.g. dimethylamine, diethylamine, dipropylamine, dibutylamine, N-methylbutylamine, N-ethylphenethylamine, pyrrolidine, piperidine, morpholine, 4-methylpiperazine).

The reaction of the present invention is carried out by treating the carboxamide (II) with the amine (III) in the presence of an alkaline hypohalite and an alkaline hydroxide. Amount of the amine (III) for the carboxamide (II) is at least about 1.0 mol equivalent, preferably about 2.0 to about 15 mol equivalent. Examples of the alkaline hypohalite are an alkali metal hypohalite such as the hypobromite and hypochlorite (e.g. sodium hypobromite, potassium hypochlorite, sodium hypochlorite, potassium hypobromite) and an alkaline earth metal hypohalite such as the hypobromite and hypochlorite (e.g. calcium hypobromite, calcium hypochlorite). Amount of the alkaline hypohalite for the carboxamide (II) is about 1.0 to about 1.2 mol equivalent, preferably about 1.0 to 1.1 mol equivalent. Examples of the alkaline hydroxide are an alkali metal hydroxide (e.g. sodium hydroxide, potassium hydroxide) and an alkaline earth metal hydroxide (e.g. calcium hydroxide). Amount of the alkaline hydroxide for the carboxamide (II) is about 0.5 to about 2.0 mol equivalent, preferably 0.7 to about 1.7 mol. The reaction can be effected in an inert solvent medium under suitable heating and if necessary, pressure. The inert solvent medium means water or a mixed medium consisting of water and organic solvent such as dimethylsulfoxide, pyridine, triethylamine, methanol, ethanol, or dimethylformamide at a free ratio. Most preferble is aqueous dimethylsulfoxide. A relative ratio of water:hydrophilic organic solvent is 100:0 to 0:100 by weight, preferably 100:0 to about 20:about 80 by weight. Reaction temperature may be adopted in the range from about 10° C. to about 200° C., preferably about 60° C. to about 120° C. Reaction pressure may be adopted in the range from about 1.0 to about 30 atmospheres. Reaction may be carried out continuously or in a batch system.

Industrial advantage in the present process consists in the fact that the product (I) is obtained in a high yield by short steps with simple operations.

Presently preferred and practical embodiments of the present invention are illustratively shown in the following examples.

EXAMPLE 1

To a solution of sodium hydroxide (0.84 g) in water (11 ml), 13.40% aqueous sodium hypochlorite (11.22 g) and 5-t-butyl-3-isoxazolylcarboxamide (3.36 g) are added under ice cooling, and the resultant mixture is stirred for 3 hours. A solution of sodium hydroxide (0.56 g) in water (3 ml) and 40% aqueous dimethylamine (4.51 g) are added thereto, and the resultant mixture is refluxed for 1 hour, while cooling the reflux condenser with dry-ice and acetone. After cooling, the reaction mixture is shaken with chloroform, and the chloroform layer is evaporated to give crude product (3.17 g). The product is chromatographed on a column of silica gel to give 1,1-dimethyl-3-(5-t-butyl-3-isoxazolyl)urea (2.29 g) as crystals melting at 119.5° to 120.5° C.

EXAMPLE 2

To a solution of sodium hydroxide (0.84 g) in water (11 ml), 13.40% aqueous sodium hypochlorite (11.22 g) and 5-t-butyl-3-isoxazolylcarboxamide (3.36 g) are added, and the resultant mixture is stirred for 3 hours under ice cooling. Then, morpholine (1.92 g) and a solution of sodium hydroxide (0.56 g) in water (3 ml) are added thereto, and the resultant mixture is refluxed for 1 hour. After cooling, the reaction mixture is shaken with chloroform, and the chloroform layer is evaporated to give crude product (0.82 g). This product is chromatographed on a column of silica gel to give N-(5-t-butyl-3-isoxazolyl)morpholinocarboxamide (2.11 g) as crystals melting at 177.0° to 180.0° C.

EXAMPLE 3

Using N-methylbenzylamine (4.84 g) in lieu of morpholine, the reaction is effected as in Example 2 to give an oil (6.92 g). This product is chromatographed on a column of silica gel to give 1-benzyl-1-methyl-3-(5-t-butyl-3-isoxazolyl)urea (3.53 g) as crystals melting at 107.0° to 108.0° C.

EXAMPLE 4

Using methylamine in lieu of dimethylamine, the reaction of Example 1 is repeated in an autoclave, whereby 1-methyl-3-(5-t-butyl-3-isoxazolyl)urea is obtained as crystals melting at 187.0° to 187.5° C. The yield is 68.5%.

EXAMPLES 5 TO 11

Using the starting carboxamide (II) and amine (III), the reactions are effected as in Example 1, whereby the corresponding products (I) are obtained.

Table 2

$$\text{(II)} \quad \xrightarrow{R^1-NH-R^2 \text{ (III)}} \quad \text{(I)}$$

| Example No. | II R | II X | III R$^1$ | III R$^2$ | I m.p. (° C.) or IR (cm$^{-1}$) |
|---|---|---|---|---|---|
| 5 | i-Pr | H | H | Me | 112.0–113.0 |
| 6 | t-Bu | H | Me | Bu | 65.5–66.5 |
| 7 | i-Bu | H | Me | Me | 69.0–70.0 |
| 8 | i-Pr | H | Me | Bu | 1680, 1616 (CCl$_4$) |
| 9 | c-Pr | H | H | Me | 157.0–158.0 |
| 10 | t-Bu | Cl | Me | Me | 155.0–156.0 |
| 11 | —(CH$_2$)$_4$— | | Me | Me | 82.5–83.5 |

Note:
The abbreviations each have the following significance: H (Hydrogen atom), Me (Methyl group), Pr (Propyl group), Bu (Butyl group), i-(iso-), t-(tertiary-), c-(cyclo-).

EXAMPLE 12

To a solution of 13% aqueous sodium hypochlorite (115.7 g) and 48% aqueous sodium hydroxide (28.3 g), 5-t-butyl-3-isoxazolylcarboxamide (33.64 g) is added, and the resultant mixture is stirred for 30 minutes. In an autoclave dimethylsulfoxide (234.4 g) and 85% aqueous dimethylamine (106.1 g) are added instantly to the mixture, which is heated rapidly up to 90° C. under stirring, and stirred for 30 minutes. After cooling, excessive dimethylamine is evaporated under reduced pressure, and pH is adjusted to 2 with 35% aqueous hydrochloric acid. The precipitated crystals are filtered, washed with dilute aqueous sodium hydroxide and water in that order, and then dried to give 1,1-dimethyl-3-(5-t-butyl-3-isoxazolyl)urea (37.0 g) as crystals. The yield is 87.5%.

What is claimed is:
1. A process for preparing a compound of the formula:

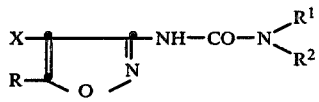

wherein R represents hydrogen, $C_1$–$C_6$ alkyl, phenyl, tolyl or xylyl; $R^1$ represents hydrogen or $C_1$–$C_6$ alkyl; $R^2$ represents $C_1$–$C_6$ alkyl, benzyl, phenethyl, phenyl, tolyl or xylyl; or

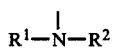

represents pyrrolidino, piperidino, morpholino or 4-alkylpiperazino; X represents hydrogen or halogen; or R and X form $C_3$–$C_5$ alkylene,
which comprises the step of reacting a carboxamide of the formula:

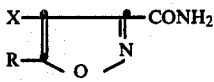

wherein R and X each is as defined above, with an amine of the formula:

$R^1-NH-R^2$ wherein $R^1$ and $R^2$ each is as defined above, in the presence of an alkaline hypohalite and an alkaline hydroxide in aqueous dimethylsulfoxide.

2. Process according to claim 1, in which the amount of the amine for the carboxamide is at least 1.0 mol equivalent.

3. Process according to claim 2, in which the amount of the amine for the carboxamide is about 2.0 to about 15 mol equivalents.

4. Process according to claim 1, in which the amount of the alkaline hypohalite for the carboxamide is about 1.0 to about 1.2 mol equivalents.

5. Process according to claim 4, in which the amount of the alkaline hypohalite for the carboxamide is about 1.0 to about 1.1 mol equivalents.

6. Process according to claim 1, in which the amount of the alkaline hydroxide for the carboxamide is about 0.5 to about 2.0 mol equivalents.

7. Process according to claim 6, in which the amount of the alkaline hydroxide for the carboxamide is about 0.7 to about 1.7 mol equivalents.

8. Process according to claim 1, in which the reaction is effected by reacting the carboxamide with at least 1.0 mol equivalent of the amine in the presence of about 1.0 to about 1.2 mol equivalents of alkaline hypohalite and about 0.5 to about 2.0 mol equivalents of alkaline hydroxide in aqueous dimethylsulfoxide.

9. Process according to claim 8, in which the reaction is effected by reacting the carboxamide with about 2.0 to about 15 mol equivalents of the amine in the presence of about 1.0 to about 1.1 mol equivalents of alkaline hypohalite and about 0.7 to about 1.7 mol equivalents of alkaline hydroxide in aqueous dimethylsulfoxide.

10. Process according to claim 1, in which 5-t-butyl-3-isoxazolylcarboxamide is reacted with dimethylamine to give 1,1-dimethyl-3-(5-t-butyl-3-isoxazolyl) urea.

* * * * *

UNITED STATES PATENT AND TRADEMARK OFFICE
CERTIFICATE OF CORRECTION

PATENT NO. : 4,212,981
DATED : July 15, 1980
INVENTOR(S) : Hisajiro Yukinaga, Shinzaburo Sumimoto, Ichiro Ishizuka, and Jitsuo Sugita It is certified that error appears in the above-identified patent and that said Letters Patent are hereby corrected as shown below:

In the heading of the Patent, in the space provided for priority information, insert the following:

--Foreign Application Priority Data

July 27, 1973  Japan ......................85339

Signed and Sealed this

Twenty-sixth Day of May 1981

[SEAL]

Attest:

RENE D. TEGTMEYER

Attesting Officer  Acting Commissioner of Patents and Trademarks